(12) United States Patent
West et al.

(10) Patent No.: US 10,279,196 B2
(45) Date of Patent: *May 7, 2019

(54) RADIATION TREATMENT PLANNING USING FOUR-DIMENSIONAL IMAGING DATA

(75) Inventors: Jay B. West, Mountain View, CA (US); John Allison, Los Altos, CA (US); John R. Dooley, Castro Valley, CA (US); Calvin R. Maurer, Jr., Mountain View, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 1678 days.

This patent is subject to a terminal disclaimer.

(21) Appl. No.: 11/540,327

(22) Filed: Sep. 28, 2006

(65) Prior Publication Data
US 2008/0081991 A1 Apr. 3, 2008

(51) Int. Cl.
*A61N 5/10* (2006.01)

(52) U.S. Cl.
CPC .......... *A61N 5/1031* (2013.01); *A61N 5/1037* (2013.01); *A61N 5/1049* (2013.01); *A61N 5/1083* (2013.01)

(58) Field of Classification Search
CPC .. A61N 5/1031; A61N 5/1083; A61N 5/1037; A61N 5/1049
USPC .................................. 378/65; 600/407, 411
See application file for complete search history.

(56) References Cited

U.S. PATENT DOCUMENTS

| | | | |
|---|---|---|---|
| 5,189,687 A * | 2/1993 | Bova | A61N 5/10 378/15 |
| 5,207,223 A | 5/1993 | Adler | |
| 5,398,684 A | 3/1995 | Hardy | |
| 6,169,817 B1 | 1/2001 | Parker et al. | |
| 6,266,062 B1 | 7/2001 | Rivara | |
| 6,307,914 B1 | 10/2001 | Kunieda et al. | |
| 7,623,679 B2 | 11/2009 | West et al. | |
| 2003/0072479 A1 | 4/2003 | Totterman et al. | |
| 2004/0034301 A1* | 2/2004 | Falco | 600/427 |
| 2004/0079899 A1* | 4/2004 | Ma | A61N 5/1042 250/492.3 |
| 2004/0092815 A1* | 5/2004 | Schweikard | A61B 6/12 600/425 |
| 2004/0254773 A1* | 12/2004 | Zhang et al. | 703/11 |
| 2004/0258286 A1* | 12/2004 | Salla et al. | 382/128 |
| 2005/0027194 A1* | 2/2005 | Adler et al. | 600/427 |
| 2005/0084140 A1 | 4/2005 | Kakadiaris et al. | |
| 2005/0143651 A1 | 6/2005 | Verard et al. | |

(Continued)

FOREIGN PATENT DOCUMENTS

WO WO 03/076003 9/2003

OTHER PUBLICATIONS

Rietzel et al., Four-Dimensional Image-Based Treatment Planning: Target Volume Segmentation and Dose Calculation in the presence of Respiratory Motion, International Journal of Radiation Oncology Biology and Physics, vol. 61, Issue 5, Apr. 1, 2005, pp. 1535-1550.*

(Continued)

*Primary Examiner* — James Kish
*Assistant Examiner* — Ellsworth Weatherby
(74) *Attorney, Agent, or Firm* — Womble Bond Dickinson (US) LLP; Daniel E. Ovanezian

(57) ABSTRACT

A method and apparatus for treatment planning using four dimensional imaging data.

31 Claims, 11 Drawing Sheets

(56) References Cited

U.S. PATENT DOCUMENTS

| | | | |
|---|---|---|---|
| 2005/0197564 A1* | 9/2005 | Dempsey | 600/411 |
| 2006/0074292 A1 | 4/2006 | Thomson et al. | |
| 2007/0076846 A1* | 4/2007 | Ruchala et al. | 378/65 |
| 2007/0167784 A1* | 7/2007 | Shekhar | A61B 6/032 600/443 |

OTHER PUBLICATIONS

Keall et al., Four-dimensional radiotherapy planning for DMLC-based respiratory motion tracking, Apr. 2005, Med. Phys., 32 (4), pp. 942-951.*

Zhang, Tiezhi, et al. "Treatment plan optimization incorporating respiratory motion." Medical physics 31 (2004): 1576.*

Keall et al. Four-dimensional radiotherapy planning for DMLC-based respiratory motion tracking, Med. Phys. 32 "4 . . . , Apr. 2005.*

Zhang et al., Treatment plan optimization incorporating respiratory motion, Med. Phys. 31 "6 . . . , Jun. 2004.*

Keall, 4-Dimensional Computed Tomography Imaging and Treatment Planning, Seminars in Radiation Oncology, vol. 14, No. 1 (Jan.), 2004: pp. 81-90.*

European Application No. 07115355.5 Office Action dated Oct. 30, 2008, 3 pages.

Rietzel E. et al., "Four-dimensional image-based treatment planning: Target volume segmentation and dose calculation in the presence of respiratory motion", International Journal of Radiation: Oncology Biology Physics, Pergamon Press, US, vol. 61, No. 5, Apr. 1, 2005, pp. 1535-1550, XP004842268, ISSN: 0360-3016.

European Search Report, EP07115355, Dec. 4, 2007, 2 pages.

E. Coste-Maniere, D. Olender, W. Kilby, R.A. Schulz, "Robotic Whole Body Stereotactic Radiosurgery: Clinical Advantages of the CyberKnife® Integrated System", The International Journal of Medical Robotics and Computer Assisted Surgery, 2005;1(2):28-39.

Paul Keall, "4-Dimensional Computed Tomography Imaging and Treatment Planning", Seminars in Radiation Oncology, vol. 14, No. 1 (Jan.), 2004: pp. 81-90.

Yuichiro Kamino, M.S., et al., "Development of a Four-Dimensional Image-Guided Radiotherapy System with a Gimbaled X-Ray Head", Int. J. Radiation Oncology Biol. Phys., vol. 66, No. 1, pp. 271-278, 2006.

Calvin R. Maurer, Jr. et al., "Hybrid point-and-intensity-based deformable registration for abdominal CT images", Medical Imaging 2005: Image Processing, edited by J. Michael Fitzpatrick, Joseph M. Reinhardt, Proc. of SPIE vol. 5747 (SPIE, Bellingham, WA, 2005), 1605-7422/05, pp. 204-211.

Communication pursuant to Article 94(3) dated Oct. 30, 2008, for EP application No. 07115355.5.

Jay B. West et al., "Hybrid Point-and-Intensity-Based Deformable Registration for Abdominal CT Images", Medical Imaging 2005: Image Processing, edited by J. Michael Fitzpatrick, Joseph M. Reinhardt, Proc. of SPIE vol. 5747 (SPIE, Bellingham, WA 2005), 1605-7422/05, pp. 204-211.

European Search Report, EP07115355, dated Dec. 4, 2007, 5 pages.

Examination Report for 07 115 355.5-2305, dated May 7, 2010.

U.S. Appl. No. 11/638,827, Restriction Requirement dated Jun. 23, 2008, 6 pages.

U.S. Appl. No. 11/638,827, Office Action dated Oct. 3, 2008, 21 pages.

U.S. Appl. No. 11/638,827, Final Office Action dated Apr. 20, 2009, 25 pages.

U.S. Appl. No. 11/638,827, Notice of Allowance dated Oct. 2, 2009, 8 pages.

Examination Report for 07 115 355.5-2305, dated Nov. 29, 2010.

\* cited by examiner

RADIATION TREATMENT PLANNING USING FOUR-DIMENSIONAL IMAGING DATA

TECHNICAL FIELD

This invention relates to the field of radiation treatment and, in particular, to treatment planning using four-dimensional imaging data.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of x-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

One challenge facing the delivery of radiation to treat pathological anatomies is identifying the target region at a particular point in time because the pathological anatomies may move as a function of the patient's breathing or other natural movements. In radiation treatment, it is useful to accurately locate and track the motion of a target region due to respiratory or other patient motions during the treatment. In order to perform radiation treatment in organs near the abdomen, for example, lungs, liver, or pancreas, it is necessary to take into account the fact that these structures move during the patient's respiratory cycle. Conventional methods and systems have been developed for performing tracking of an internal target region, while measuring and/or compensating for breathing and/or other motions of the patient.

In one conventional method, instead of prescribing a dose solely to the target region, a margin around the target region is defined so that the entire volume traversed by the target region during free breathing receives the prescription dose. Another conventional method controls the amplitude of the patient's respiration, for example, by using a restraint on the chest, so that tissue movement is reduced. A treatment margin is defined, but in this case a smaller treatment volume is used to reflect the reduced amplitude of motion.

Yet other conventional methods utilize breath holding and respiratory gating to compensate for target region movement during respiration while a patient is receiving conventional radiation treatments. Breath holding requires the patient to hold their breath at the same point in each breathing cycle, during which time the tumor is treated while it is presumably stationary. A respirometer is often used to measure the tidal volume and ensure the breath is being held at the same location in the breathing cycle during each irradiation moment. This method takes a relatively long time and often requires training the patient to hold their breath in a repeatable manner.

Respiratory gating involves a process of measuring the patient's respiratory cycle during treatment and then turning the radiation beam on only for a predetermined part of the patient's breathing cycle. Respiratory gating does not directly compensate for motions that result from breathing. Rather, radiation treatment is synchronized to the patient's breathing pattern, limiting the radiation beam delivery to times when the tumor is presumably in a reference position. Respiratory gating may be quicker than the breath holding method, but also may require the patient to have many sessions of training over several days to breathe in the same manner for long periods of time. Conventional respiratory gating also may expose healthy tissue to radiation before or after the tumor passes into the predetermined position. This can add an additional margin of error of about 5-10 millimeters (mm) on top of other margins normally used during treatment. However, the prescription volume can usually be smaller than that using free breathing without gating. These conventional methods are limited by the patient's ability to perform breathing functions in a consistent manner over multiple treatment sessions.

Another conventional method of dealing with the motion of a target region during radiation treatment involves the image tracking of fiducial markers that are placed in or near the target region. The position and motion of the fiducial markers is correlated with the position and motion of the target region so that real-time correction of the position of the treatment beam to follow the motion of the target region may be realized.

Each of these techniques has its advantages and drawbacks. Without restraint or gating, a fast treatment is possible that is comfortable for the patient. However, especially in regions where respiratory motion is large, for example, near the diaphragm, this approach necessitates the irradiation of a volume of tissue substantially larger than the target region. Controlling respiratory amplitude can make treatment uncomfortable, and gating causes an increase in treatment time. Performing real-time correction according to the movement of fiducial markers implanted in the target region allows a conformal dose distribution to be delivered quickly. Nevertheless, this method does have a disadvantage that it requires invasive fiducial implantation. Real-time correction according to the movement of fiducial markers also requires a radiation delivery device that can be moved quickly and accurately. One such radiation treatment system is the CYBERKNIFE® system developed by Accuray Incorporated of California. By mounting a compact X-band linear accelerator on a robot arm assembly, the CYBERKNIFE® radiation treatment system can perform real-time compensation for respiratory motion.

One conventional treatment planning approach using a CYBERKNIFE® radiation treatment system utilizing inverse planning techniques is as follows. First, a target region and critical structures to be avoided are delineated on a CT scan, or a set of CT slices of a volume of interest (VOI) in the patient. More specifically, a three-dimensional (3D) CT scan is composed of a three-dimensional model of a volume of interest (e.g., pathological anatomy bearing portion of the body) generated from a collection of two-dimensional (2D) CT slices, with each slice representing a different position in space (for example, a different position along the inferior-superior axis of the patient). In CT scanning, numerous x-ray beams are passed through a volume of interest in a body structure at different angles. Then, sensors measure the amount of radiation absorbed by different tissues. As a patient lies on a couch, an imaging system records x-ray beams from multiple points. A computer program is used to measure the differences in x-ray absorption to form cross-sectional images, or "slices" of the head and brain. These slices are called tomograms; hence the name "computed tomography."

Once the target region and critical structures have been delineated, dose constraints may then be applied by a medical physicist to these target regions and critical structures. The medical physicist specifies the minimum dose, and optionally the maximum dose, to the tumor and the maximum dose to other healthy tissues independently. The treatment planning software then selects a set of treatment beam parameters (e.g., direction, total number of beams and energy of the beams) in order to achieve the specified dose constraints. Next, the dose constraints may be altered, tuning structures may be added, and the treatment plan re-optimized until the dose distribution is acceptable. The finalized treatment plan is then sent to a treatment delivery system.

One article entitled, 4-Dimensional Computed Tomography Imaging and Treatment Planning, Paul Keall, Seminars in Radiation Oncology, Vol 14, No 1 (January), 2004; pp 81-90, discusses the idea of radiotherapy planning using a 4D CT image. The planning optimization step is described in this article as a set of separate 3D optimization steps performed on each of the 3D CT images making up the 4D CT.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

It should be noted in particular that although discussed at times herein in regards to a robotic-based, image guided radiation treatment system, the methods herein may also be used with other types of radiation treatment systems such as a gantry based radiation delivery system. It should also be noted that the methods and apparatus are discussed herein in relation to CT imaging only for ease of explanation. The method and apparatus discussed herein may also be used to develop treatment plans using other types of four dimensional (4D) medical diagnostic images (anatomical and/or functional), for example, magnetic resonance (MR), ultrasound (US), nuclear medicine (NM) positron emission tomography (PET) and single photon emission computed tomography (SPECT), etc. In addition, the "target regions" discussed herein may include an anatomical feature(s) of a patient such as a pathological or normal anatomy and may include one or more non-anatomical reference structures. Alternatively, a target region need not include an anatomical structure in embodiments outside the field of medical diagnostic imaging and patient treatment.

Figure 1A:
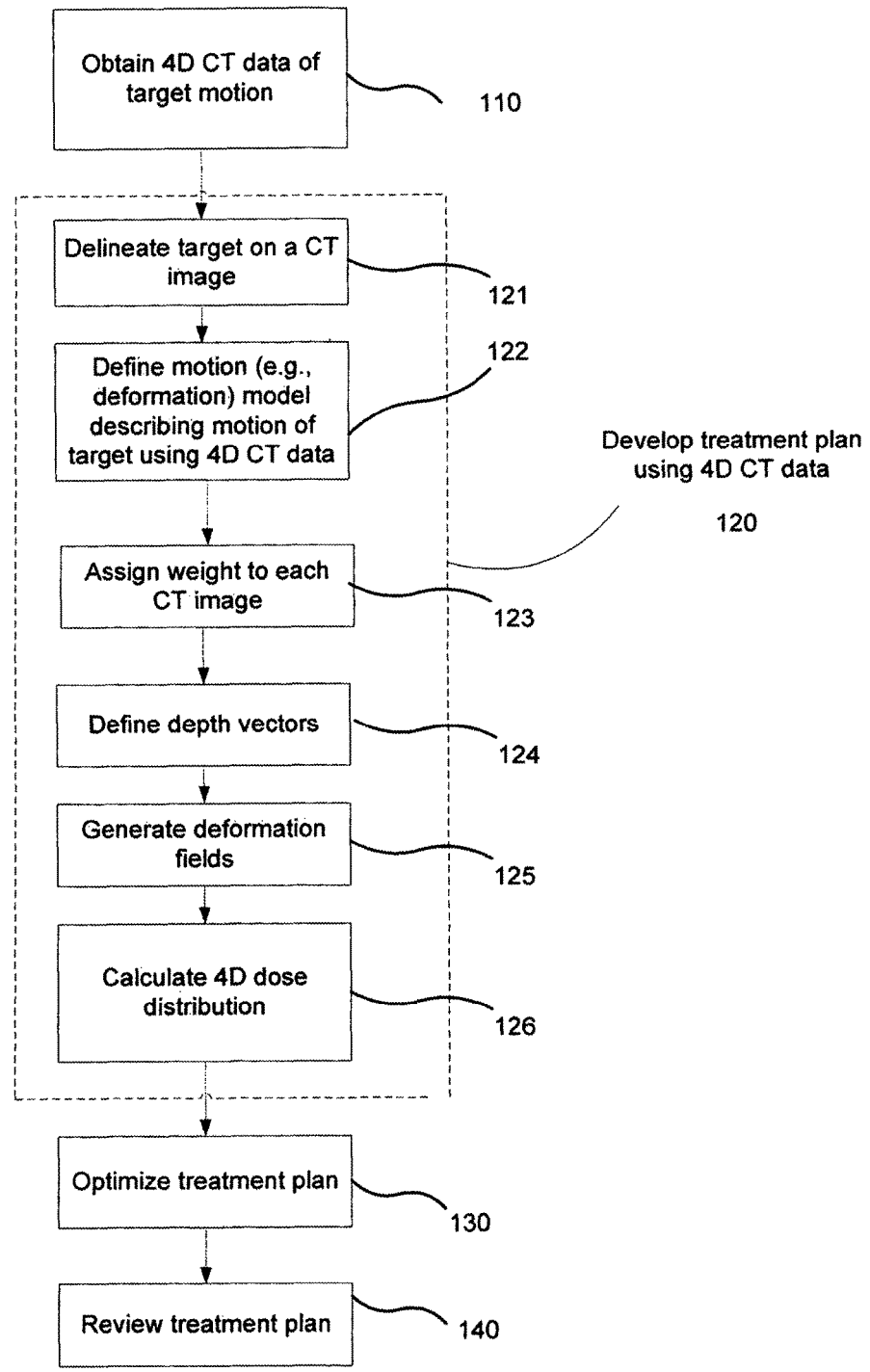
FIG. 1A illustrates a method of radiation treatment planning according one embodiment of the present invention.

FIG. 1A illustrates a method of radiation treatment planning according to one embodiment of the present invention. The method of the present invention includes obtaining four-dimensional (4D) CT data 110 of the motion, including translation, rotation, and deformation, of the target region and surrounding structures, and developing a treatment plan using the four-dimensional CT data 120. The four-dimensional CT scan data may be imported into a treatment planning system or may already reside on a diagnostic CT imaging system that is also used for treatment planning system that was used to perform the diagnostic 4D CT imaging. The treatment planning system may be fully compliant with DICOM standards for the distribution and viewing of medical images and the DICOM-RT standard for viewing radiotherapy information overlain on medical images.

Figure 1B:
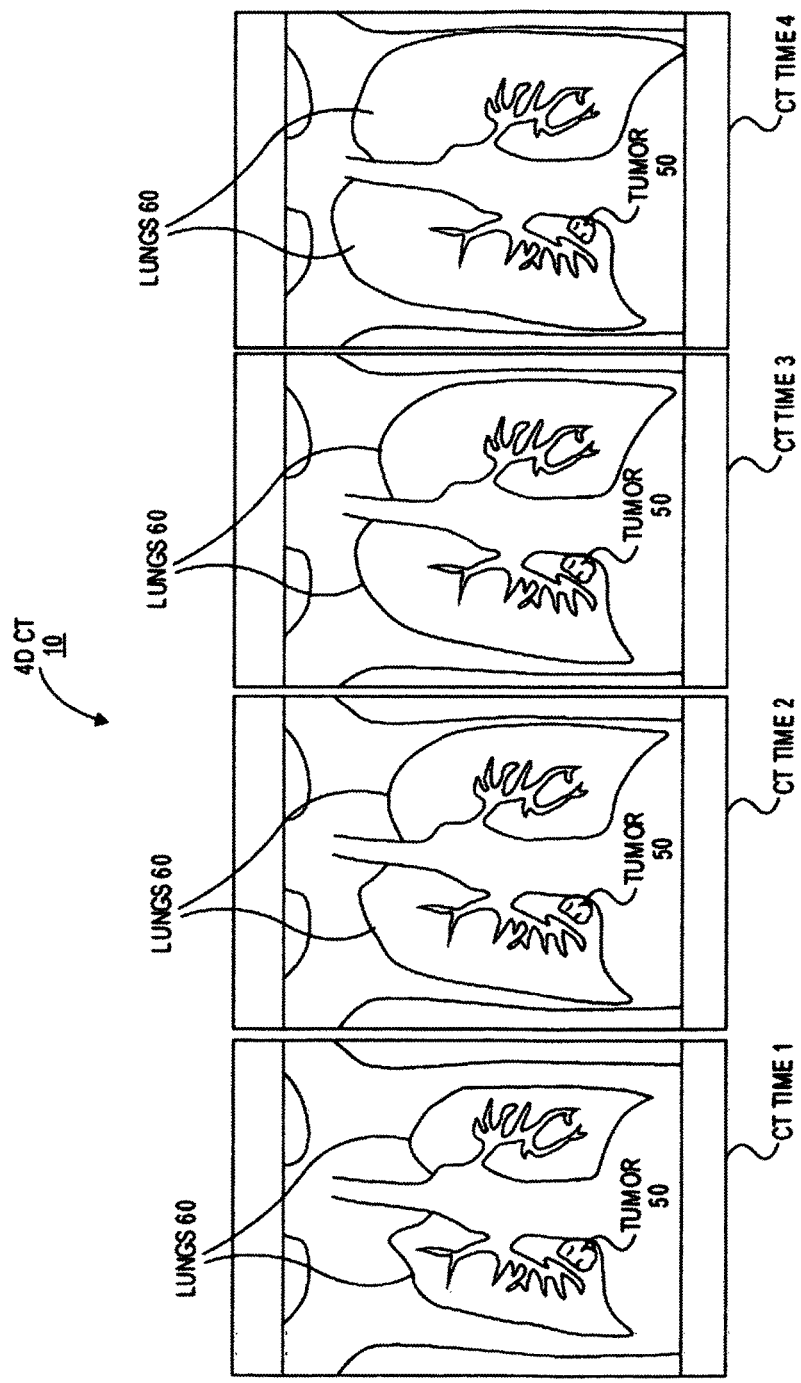
FIG. 1B is a conceptual illustration of a 4D CT scan.

It should be noted that the four dimensions refer to three spatial dimensions and one temporal dimension, as opposed to four spatial dimensions. More specifically, the 4D CT scan data is a collection of three dimensional (spatial) images, with each of the three dimensional images taken at a different point in time in a motion cycle (e.g., during the respiratory cycle, cardiac cycle, artery pulsation, etc. of a patient) with known temporal relationship. FIG. 1B is a conceptual illustration of a 4D CT scan of a patient's chest region including lungs 60 and a target tumor 50. The exemplary 4D CT scan 10 of FIG. 1B includes four 3D CTs taken a four time points in the patient's respiratory cycle: CT Time 1, CT Time 2, CT Time 3 and CT Time 4. Each of the 3D CT scans has an index associated with it describing a subset of the respiratory cycle, for example, splitting the cycle into index 0 (time 1)=full exhale, index 100 (time 4)=full inhale and two intermediate indexes for time 2 and time 3. As can be seen from an inspection of the images in FIG. 1B, tumor 50 is, for this example, displaced and deformed in the CT image at time 4, full inhale, relative to its positions and shape at full exhale in CT image at time 1.

In one embodiment, the 4D CT scan data may be generated using a 4D CT scanner, for example, a 4D CT scanner produced by General Electric Corp. Alternatively, other 4D CT scanners may be used. A 4D CT scanner includes a device, such as a spirometer, strain gauge, optical tracker, etc., that is configured to take instantaneous measurements of the patient's position in the respiratory cycle. When a slice is acquired, the current respiratory measurement position is recorded. This measurement is used to place the CT slice in one of the 3D CT scans with the index closest to the given measurement of the respiratory cycle. While with 3D CT scans, some subsets of slices may be acquired simultaneously, there is not attempt to index the timing of the slice acquisition to physical processes, e.g., the breathing cycle, other than in optionally halting the breathing cycle by instructing the patient to cease breathing while the scan is taken.

The 4D CT scan data may be acquired in a single motion cycle, or may be acquired over multiple motion cycles. In another embodiment, two or more conventional 3D CT images may be acquired during breath hold at different points in the breathing cycle (e.g., at end inspiration and end expiration. Accordingly, the term 4D CT scan data is used herein to mean a set of two or more 3D images that represent different time points in a motion cycle regardless of the method of acquiring the scan data.

Figure 2:
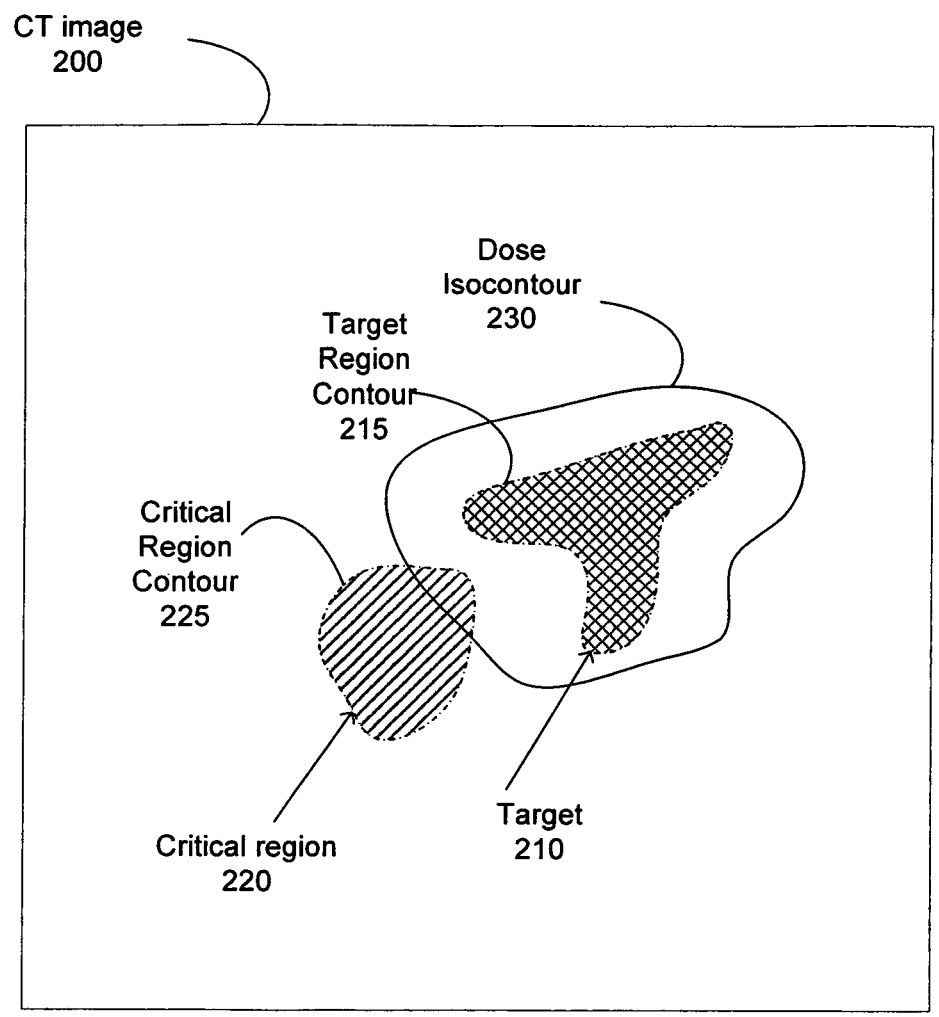
FIG. 2 illustrates a graphical output of a treatment planning software displaying a slice of a CT image.

In step 121, the target region is delineated on a CT image, for example, as illustrated in FIG. 2 as will be discussed in more detail below. In one embodiment, one of the 4D CT images may be used for delineation of the target region and critical structures. Alternatively, delineation may be performed using a standard CT image acquired with breath hold (i.e., a patient holding their breath). In yet another embodiment, delineation may be performed on an image of a different modality, for example, using magnetic resonance imaging (MRI.) Referring still to FIG. 1A, next, a motion (e.g., deformation) model is defined so that the movement of target region and surrounding structures within the treatment region is known, step 122. The model may be defined, for example, using non-rigid registration techniques. Non-rigid registration techniques are well known in the art; accordingly, a more detailed discussion is not provided.

A dose distribution is then calculated using the motion model, step 126. When the dose distribution is calculated, the motion model, together with a weighting (as discussed in further detail below) according to the relative amount of time spent at each point in the motion cycle, is applied to give a dose estimate taking motion (e.g., due to respiration) into account. In this way, a view of the treatment dose that takes into account motion movement during treatment may be obtained. The treating physician or physicist may then use this dose information to change the treatment margins and/or re-optimize the treatment plan, step 130, if desired. The treatment plan may also be reviewed after optimization to view effects of the target region motion on the dose distribution, step 140. Further details of embodiments of the method steps of FIG. 1A are provided below.

FIG. 2 is a conceptual illustration of a graphical output of a treatment planning system displaying a slice of a CT image in which delineation may be performed. The illustration of the CT image 200 includes a target (e.g., pathological anatomy such as a tumor, lesion, vascular malformation, etc.) 210 that is targeted for treatment, and well as a critical region 220 that is positioned near the target region. The treatment planning software enables the generation of a critical region contour 225 around the critical region 220 and a target region contour 215 around the target region 210. A user manually delineates points (e.g., some of the dots on the contour lines of FIG. 2) on the display that is used by the treatment planning software to generate the corresponding contours. Based on specified minimum dose to the target region 210 and the maximum dose to the critical region 220, the treatment planning software generates the dose isocontour 230 for the target region 210. The dose isocontour 230 represents a given dose percentage (e.g., 60%, 70%, 80%, etc.) of a specified prescription dose for the target region 210. Ideally, the dose isocontour 230 should perfectly match the contour of the target region 210. However, in some cases, the dose isocontour 230 generated by the treatment planning software is not optimal, and can include portions of the critical region 220, as illustrated in FIG. 2.

Figure 3:
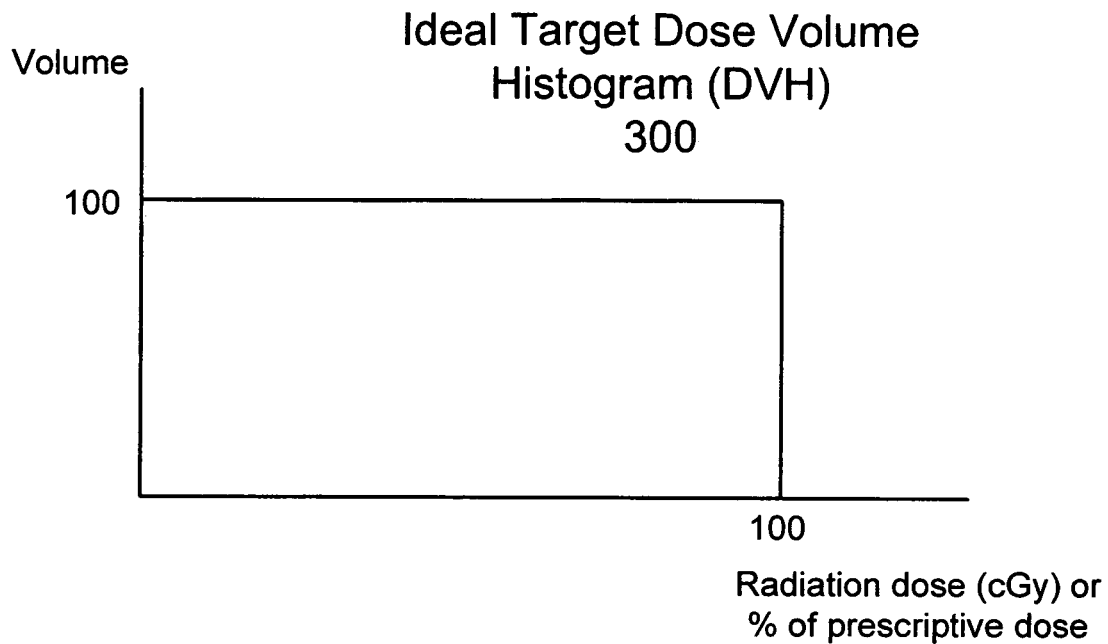
FIG. 3 illustrates an ideal DVH for a pathological anatomy.
Figure 4:
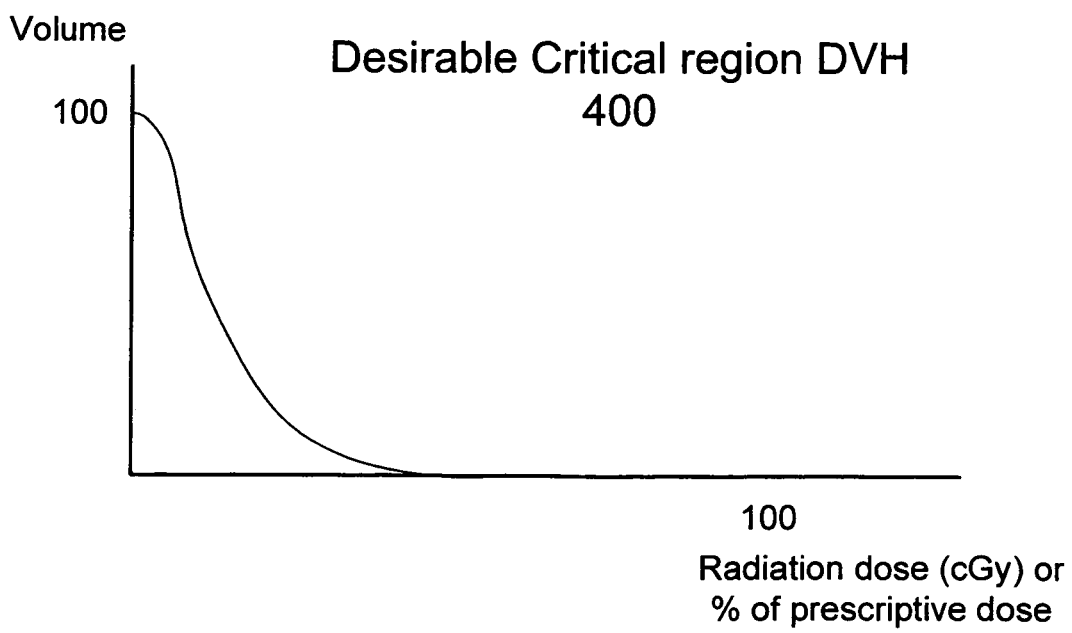
FIG. 4 illustrates one embodiment of a desirable DVH for a critical region.

The two principal requirements for an effective radiation treatment system are homogeneity and conformality. Homogeneity is the uniformity of the radiation dose over the volume of the target region characterized by a dose volume histogram (DVH). An ideal DVH 300 for the target region 210 would be a rectangular function as illustrated in FIG. 3, where the dose is 100 percent of the prescribed dose over the volume of the target region 210. In an ideal case, the dose would also be zero elsewhere. A desirable DVH 400 for a critical region 220 would have the profile illustrated in FIG. 4, where the volume of the critical structures receives as little of the prescribed dose as possible. Conformality is the degree to which the radiation dose matches (conforms to) the shape and extent of the target region (e.g., tumor) in order to avoid damage to critical adjacent structures. More specifically, conformality with respect to a target region VOI is a measure of the amount of the region receiving the prescription (Rx) dose or more, that is contained within the VOI. Conformality may be measured using a conformality index (CI)=(total volume at ≥Rx dose)/(target volume at ≥Rx dose). Perfect conformality results in a CI=1. With conventional radiotherapy treatment, using treatment planning software, a clinician identifies a dose isocontour for a corresponding VOI for application of a treatment dose (e.g., 3000 cGy).

Figure 5:
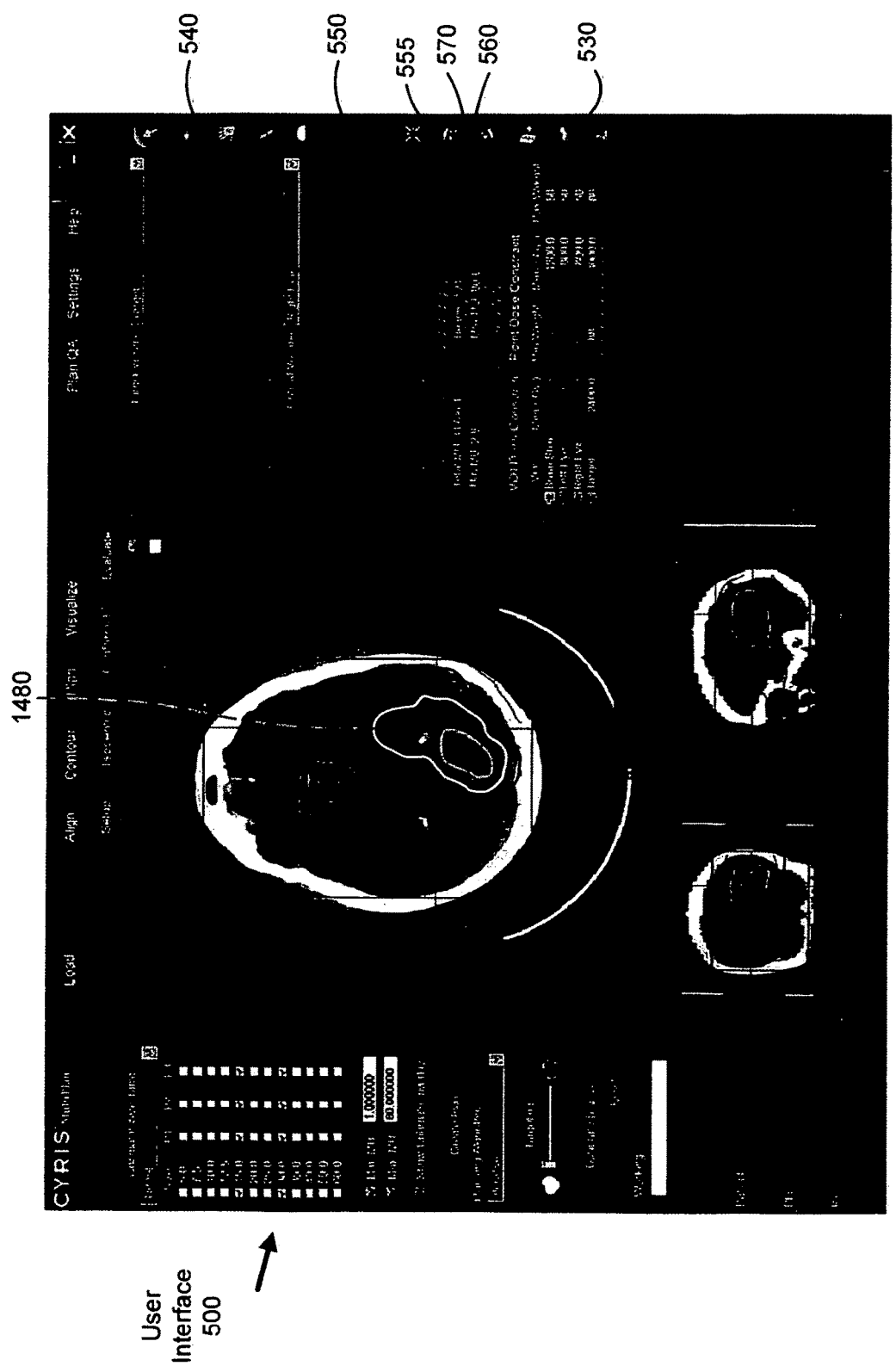
FIG. 5 is a graphical representation of an exemplary dose distribution diagram correlating predicted radiation dose to the relative locations of a target region and a critical structure.

Once the target region and avoidance structures have been delineated, step 121 of FIG. 1A, then the dose constraints may be applied to these structures as illustrated in FIG. 5. FIG. 5 illustrates one embodiment of a user interface for treatment planning system. Using the treatment planning interface 500, the user may define a minimum dose constraint for the target region 210 and a maximum dose constraint for a critical region 220. For example, a minimum dose constraint of 2400 cGy is set for the target region and a maximum dose constraint of 1200 cGy is set for the right eye critical region shown in box 530 FIG. 5. Near the right side of the user interface of FIG. 5 are a target volume DVH 540 and a critical volume DVH 550. For example, the top DVH corresponds to the target region and the bottom DVH corresponds to the right eye critical region. The user interface 500 may also display beam statistics in box 555, for example, the total MU 560 and number of beams 570, the minimum non-zero MU of all currently existing beams and the maximum MU.

A treatment plan may be developed and optimized by enabling a planning algorithm to select a set of treatment beam parameters (e.g., direction, total number of beams and energy of the beams) to best satisfy the dose constraints. The user interface 500 may also display some of these beam statistics, box 555, for example, the total MU 560 and number of beams 570, the minimum non-zero MU of all currently existing beams and the maximum MU.

Figure 6:
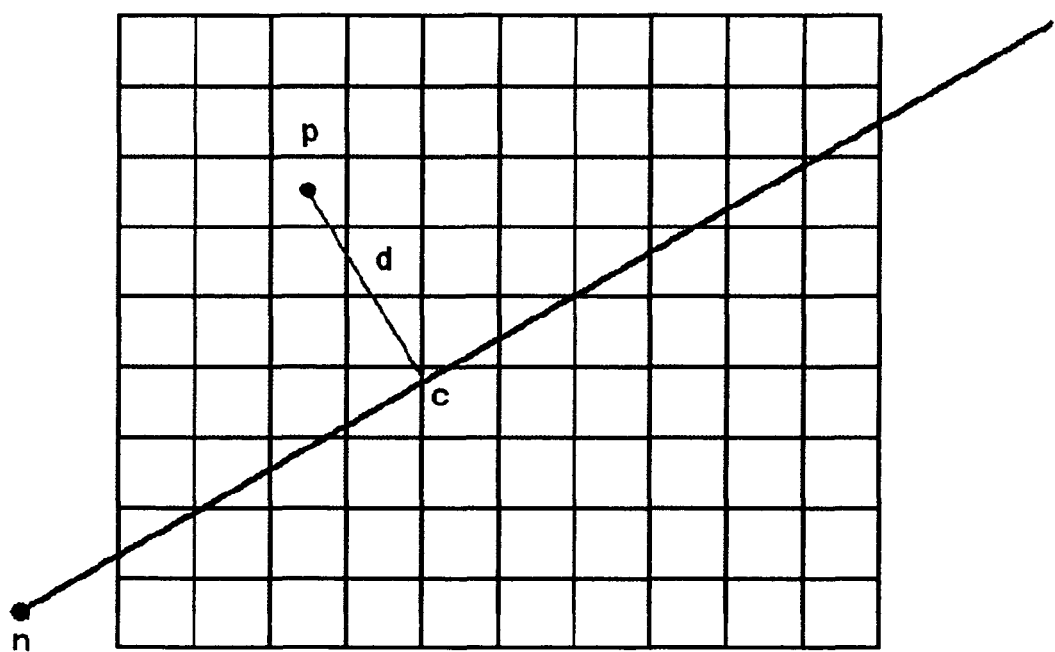
FIG. 6 illustrates one embodiment of a geometry used for dose calculation at the center of a dose volume voxel.

FIG. 6 illustrates one embodiment of a geometry used for dose calculation at the center of a dose volume voxel. The center of a voxel is represented as a position "p." The closest point to p on the beam axis is represented as "c." The point of origin of the beam is represented as "n." The distance from p to c is "d." It should be noted that FIG. 6 is an illustration of a 2D dose calculation geometry. Alternatively, a 3D geometry may be constructed, for example, by using a 3D grid instead of the 2D grid shown in FIG. 6.

Dose calculation, without motion accounting, may be performed using a mass data storage model to calculate the radiation dose to tissue from the treatment beams from the various different parameters that are run through by the planning algorithm. In such an embodiment, an array of effective depth is constructed along each beam axis, using the CT number of the tissues the beam passes through, together with a model relating the CT number to electron density. In one embodiment, the following simplifying assumptions may be made: (1) all energy is deposited locally, i.e., charged particle equilibrium is assumed; and (2) the effective depth of tissue between the collimator and the calculation point p is the same as the effective depth between the collimator of the radiation beam source and the corresponding point c on the beam axis. Dose may be discretized by dividing the dose calculation volume into volume pixels, or voxels. For each voxel, the dose with respect to each treatment beam is calculated and added. The equation for radiation dose for a single beam is:

$$D(p) = MU \times OP(s) \times TMR(s,e(c)) \times OCR(d,s,e(c)) \times (800/|nc|)^2, \quad (1)$$

where D(p) is the radiation dose in cGy delivered by the beam to point p, MU is the number of monitor units of the beam (linearly related to the amount of time for which the beam is enabled), OP is the output factor, TMR is the tissue maximum ratio, OCR is the off-axis correction ratio, s is the field size, d is the distance of p from the beam central axis, and e(c) is the effective depth of tissue between the collimator and c.

Figure 7:
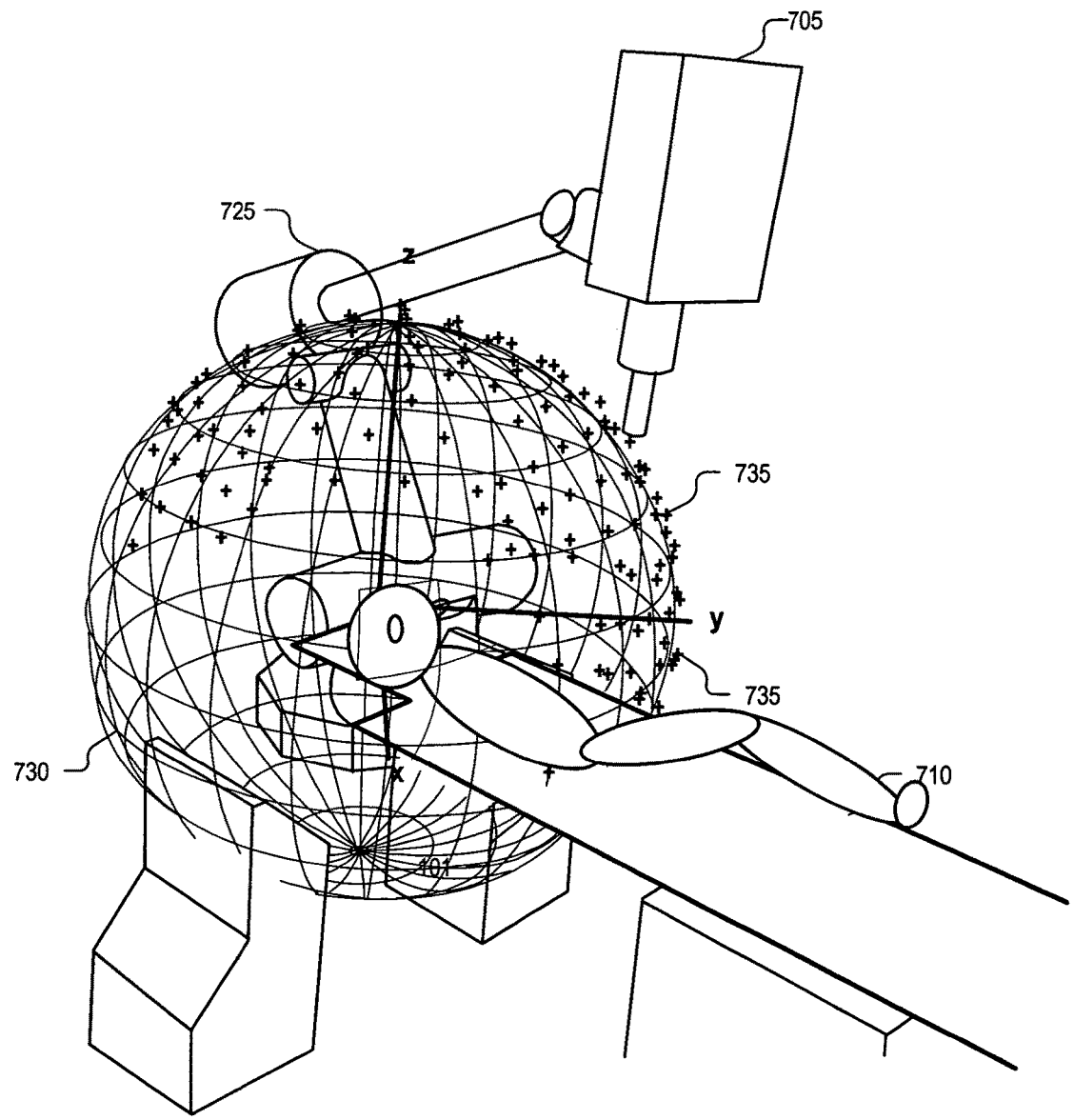
FIG. 7 is a perspective drawing illustrating a workspace of a radiation treatment delivery system including a set of spatial nodes at which to position the radiation source, in accordance with an embodiment of the present invention.

Once the dose has been calculated, it may be represented using a dose mask architecture. A dose mask is a representation where each beam has a mask: the mask elements each represent a distinct spatial position and the amount of dose per MU contributed by the beam at that position. In an exemplary embodiment, an inverse planning algorithm may be used that starts with approximately 1200 candidate beams. This set of beams may have on the order of 100 distinct points of origins, which may be referred to as nodes, which are discrete positions traversed by the radiation source that generates the beam during treatment. In one embodiment, these nodes make a shape somewhat like a hemispherical shell 730 surrounding a portion of the patient 110 (e.g., the head) as illustrated in FIG. 7. Alternatively, the nodes may form other geometries (e.g., elliptical).

It should be noted that equation (1) provided above is just one example of a dose calculation methodology. Other methodologies for calculating the dose delivered by a radiation beam to a single point, for example, superposition convolution and Monte Carlo simulation, are well known in the art and may alternatively be applied to derive D(p).

Spatial nodes 735 are represented by the "+" symbol (only a few are illustrated) in FIG. 7 and indicate positions where radiation source 705 is allowed to stop and delivery a dose of radiation to the VOI within the patient. During delivery of a treatment plan, in one embodiment, a robotic arm 725 may be used to move radiation source 705 to each and every spatial node 735 following a predefined path. Alternatively, other types of mechanisms such as a gantry may be utilized to move radiation source 705. Even if a particular treatment plan does not call for delivery of a dose of radiation from a particular spatial node 735, radiation source 705 may still visit that particular spatial node 735. It should be appreciated that the complete node set may include more or fewer spatial nodes 735 than is illustrated or discussed.

Figure 8:
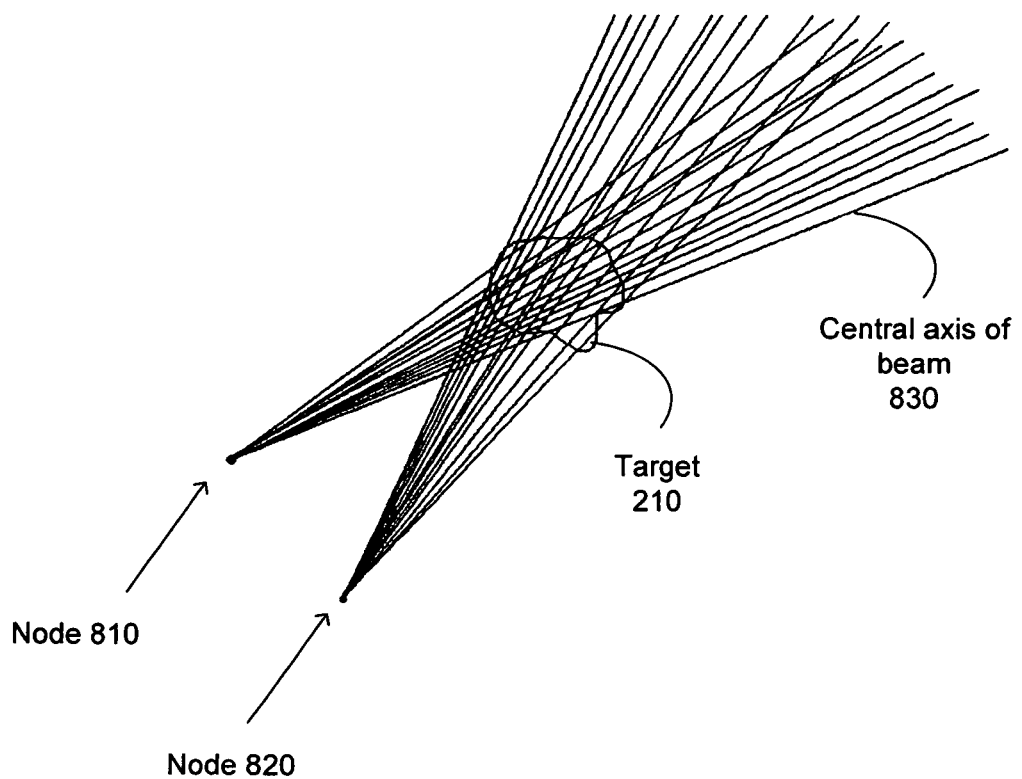
FIG. 8 illustrates two nodes contributing candidate beams for optimization according to one embodiment of the present invention.

Each node 735 may contribute multiple beam orientations to the treatment planning set of beams. FIG. 8 illustrates two nodes 810 and 820 of a node set, with each of the nodes contributing an exemplary 12 candidate beams for optimization. Only the central axis of each of a beam 830 is shown in FIG. 8. However, each beam will contribute dose in a three dimensional (e.g., conical) region centered around its axis. In the embodiment illustrated in FIG. 8, the candidate beams at nodes 810 and 820 are representative of beam delivery based on conformal planning, in which the radiation beams pass through or terminate at various points within the target region. In conformal planning, some radiation beams may or may not intersect or converge at a common point in three-dimensional space. In other words, the delivered radiation beams may be non-isocentric in that the beams do not necessarily converge on a single point, or isocenter. This may be more readily seen in the three-dimensional perspective view of FIG. 9, where the exemplary beams 901, 902, 903 and 904 intersect with target region 210, and possibly each other, but do not converge on a single point.

In this exemplary embodiment, the beam geometry is created by choosing 12 random points either on the periphery or internal to the treatment target region. In order to perform optimization of the beam weights (as discussed in further detail below), it is necessary to know how much dose is given per unit time by each beam to every voxel in the dose volume. Hence, for each beam, the results of the computation described above in equation (1) are stored as a linked list composed of elements giving location (index of the dose volume voxel) and dose per unit time at that location.

In order to define a motion (e.g., deformation) model, a CT image is designated to be a reference image. A position in the reference CT image is denoted as $x_0$. Suppose there are N additional CT images making up the 4D CT set. A set of vectors $\{\Delta_1(x_0) \ldots \Delta_N(x_0)\}$ is derived so that $x_0+\Delta_i$ represents the same anatomical point in image i as $x_0$ in the reference image. A set of third-order B-splines and an intensity-based cost function is used to find a set of deformation fields $\Delta_i(x)$. An exemplary intensity-based cost function that may be used is described in J. B. West, C. R. Maurer, Jr., and J. R. Dooley, "Hybrid point-and-intensity-based deformable registration for abdominal CT images," Medical Imaging 2005: Image Processing Proc. SPIE 5747, pp. 204-211. Alternatively, other intensity-based cost functions may be used.

Having defined the motion model in step 122, a weight, $W_i$; $\Sigma_i W_i = 1$, is assigned to each image, step 123. The $W_i$ model is the relative time spent by the target region in each part of the motion cycle. The motion cycle refers to any movement, rotation, and/or deformation of the target region and nearby structures that is periodic in nature, for example that caused by respiration. More radiation dose will be absorbed during the parts of the cycle that take up the most time. Where the motion is due to breathing, the $W_i$ may be calculated, for example, using a standard table or formula describing the relative amount of time spent by a typical person in different phases of the respiratory cycle. Alternatively, the $W_i$ may be derived from a priori breathing data measured for the particular patient. Similar where the motion is due to other factors (e.g., cardiac motion), $W_i$ may be derived from corresponding motion (e.g., cardiac) data measured for the particular patient.

For some CT scanners, such as the 4D CT scanner produced by the General Electric Corporation, the images making up the 4D CT set are separated into equal time intervals, rather than equal motion intervals. In this case, $W_i=1/N$ is used for all i, where N is the number of images making up the 4D CT set. Alternatively, if the images making up the 4D CT are separated into unequal, but known, time intervals, the $W_i$ may be proportional to the size of the time interval for each image i, and normalized so that the sum of the $W_i$ is equal to 1. For each beam, an effective depth vector $V_i$ along the central axis of the beam is derived for each image i, step 124. When deriving $V_i$, note may be taken of the movement of the beam to follow a fiducial centroid, or other landmark, if there is a dynamic target tracking method to be used during treatment. Dynamic target tracking is known in the art; accordingly, a more detailed description is not provided. Dynamic target tracking techniques are discussed, for example, in U.S. Pat. No. 5,207,223. Alternatively, other dynamic tracking techniques may be used.

In this case, both the source and target coordinates of the beam may be incremented by the offset of the object being tracked, to mimic the effect of dynamic tracking during treatment. Hence, in one embodiment, three steps are required before a 4D dose distribution is calculated: define the depth vectors $V_i$ according to predicted movements of the beams during treatment (for example, if the dynamic target tracking method is to be used), step 124; define the $W_i$ which describe the relative amounts of time the patient is predicted to spend in each part of the respiratory cycle, step 123, and; generate the deformation fields $\Delta_i$, step 125, for example, by using a non-rigid registration technique. It should be noted that steps 123, 124 and 125 need not be performed in the order illustrated in FIG. 1A. When steps 123 through 125 have been completed, a 4D dose calculation may be performed, step 126, that takes respiratory motion into account as follows:

$$D_i(p)=W_i \times MU \times OP(s) \times TMR(s,e_i(c)) \times OCR(p+\Delta_i(p),s,e_i(c)) \times (800/|nc|)^2, \quad (2)$$

where $D_i(p)$ is the dose, in cGy, given by the beam to point p during part i of the breathing cycle. Note that in Equation (2), deformation is taken account of in two ways. In all places that effective depth e is used, we replace it with the quantity $e_i$, i.e., the effective depth looked up from central axis vector $V_i$. This takes into account the fact that the amount and types of tissue traversed by the beam may change as the body deforms, and the beam is moved to track the target, thus leading to a variation of the attenuation effect at the target point. The more dominant effect in most cases, however, is the fact that the off-axis correction ratio (OCR) has been modified to take into account the amount of deformation. For example, a point that is close to the beam axis at one point in the respiratory cycle may move further away at another-point in the cycle. If the amount of movement is significant with respect to the cross section of the beam (e.g., conical beams that have a diameter of between 5 mm and 60 mm at 800 mm from the radiation source), the radiation dose may be substantially changed. Generally, this second effect is much more significant in terms of modeling the change of radiation dose. It should be noted also that the coordinate system in which the $\Delta_i$ are represented may be easily changed. In the situation described above, where the beams are being moved in order to dynamically track an object, e.g., the centroid of a fiducial configuration, we may refer the $\Delta_i$ to this coordinate system by simply subtracting the offset describing the tracking motion from each $\Delta_i$ (in intuitive terms, if a point is moved 10 mm upwards relative to a beam due to tissue deformation, but the beam is also moved 10 mm upwards in order to track the target, effectively the point has not moved relative to the beam). Having calculated the $D_i$, we may calculate $D(p)$ as $D(p)=\Sigma_i W_i D_i(p)$.

In the above formulation, the dose calculation is all referred to a reference coordinate system: that of the CT image designated to be the reference image. Hence, for each beam, we may construct a dose mask using the motion model as described above, or we may calculate a standard dose mask using only the reference image and no motion model.

As noted in FIG. 1A, an optimization step 130 may be performed after generation of the motion model. The optimization step takes into account the target region motion (e.g., deformation) and change in dose distribution during the motion cycle (e.g., respiration). The optimization process determines a set of treatment beam parameters (a set of beams, the position and orientation of each beam, the field size and optionally shape of each beam, and the relative or absolute quantity of radiation of each beam) such that the dose distribution produced by this set of treatment beam parameters optimizes a set of user-specified dose constraints (minimum and optionally maximum dose to the target region and the maximum dose to different healthy tissues). To optimize for the effect of motion, the field size and shape of each beam, and the quantity of radiation of each beam, may vary with the time point in the motion cycle. Various optimization algorithms such as an iterative algorithm and non-iterative algorithm may be used. With either an iterative algorithm or non-iterative (e.g., Simplex algorithm), a set of dose masks giving discretized estimates of dose/MU for each beam may be used as input. A set of dose constraints input by the user to determine the desirable dose distribution for that planning task may also be provided to the treatment planning algorithm. Hence, the optimization step 130 is not affected by whether or not a motion model was used to build the dose masks. However, in the case that a motion model was taken into account, the resulting dose distribution will automatically have been optimized using the known characteristics of the target region motion and beam motion during the motion cycle. It should be noted that optimization algorithms such as an iterative algorithm and Simplex algorithm are known in the art; accordingly, a more detail discussion is not provided.

Although the method of the present invention is discussed above in regards to inverse, or conformal, planning, part or all of the treatment plan may be developed using forward planning techniques. In forward planning, the user of the treatment planning system (e.g., medical physicist) chooses the directions of the beams and the intensity of the beams and then the treatment planning algorithm calculates and displays the resulting dose distribution. More specifically, the user may specify particular directions and intensities for the radiation beams to be generated by the radiation treatment delivery system, choosing from a subset of available beams determined by constraints on the delivery system itself. The user may "guess" or assign, based on their experience, values to beam directions and intensities, or weights. The treatment planning system then calculates the resulting dose distribution. By evaluating the dose distribution, the user may manually change their selection of beams in an attempt to improve the dose distribution. The feedback given to the user is the dose profile corresponding to the current plan where beams may be removed, changed or added until the dose profile is deemed acceptable. After reviewing the resulting dose distribution, the user may adjust the values of the treatment parameters. The system re-calculates a new resulting dose distribution. This process may be repeated, until the user is satisfied by the resulting dose distribution, as compared to a desired distribution.

In one embodiment, a review step 140 of FIG. 1A is performed after optimization, in order to view the effects of motion (e.g., deformation) on the dose distribution of a treatment plan optimized using a single image. To do so, a motion (e.g., deformation) model using a 4D CT set is constructed and the beam dose masks using the beam geometry and weighting (MU per beam) from the original plan is recalculated. In this way, the DVHs and dose isocontours for the original plan and its 4D recalculated version may be viewed side-by-side, so that a physician or physicist may make a determination about whether the motion will have any clinical effect on the outcome of the plan delivery. In the case that the answer is "yes" or "possibly," the next step may then be to return to the planning step and re-optimize using the updated dose information.

Figure 10:
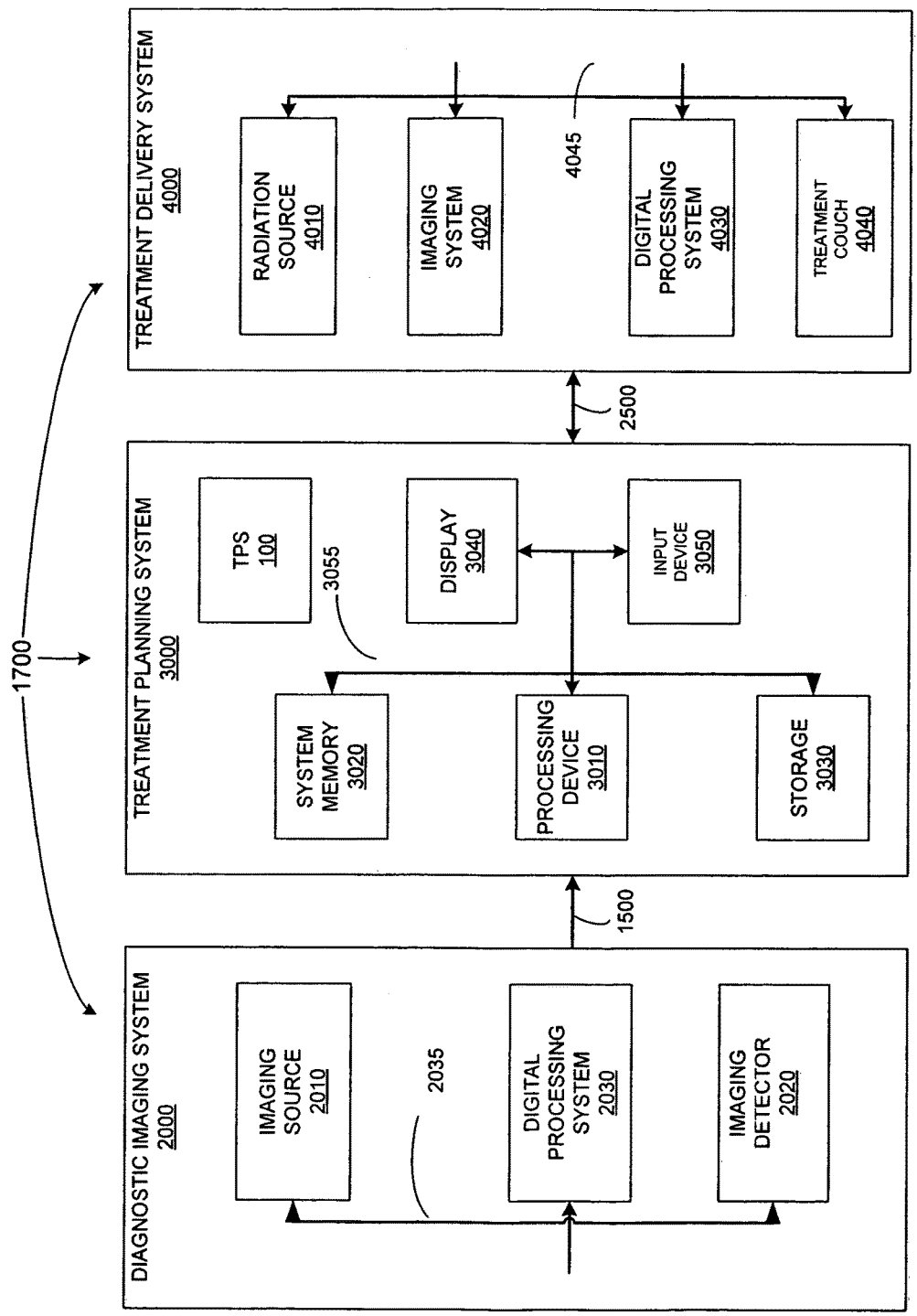
FIG. 10 illustrates one embodiment of a treatment system 1700 that may be used to perform radiation treatment in which embodiments of the present invention may be implemented.

FIG. 10 illustrates one embodiment of a treatment system 1700 that may be used to perform radiation treatment in which embodiments of the present invention may be implemented. The depicted treatment system 500 includes a diagnostic imaging system 2000, a treatment planning system 3000, and a treatment delivery system 4000.

Diagnostic imaging system 2000 is representative of a system capable of producing medical diagnostic images of a VOI that may be used for subsequent diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 is discussed at times in relation to a CT x-ray imaging modality. However, other imaging modalities such as those above may also be used.

Diagnostic imaging system 2000 includes an imaging source 2010 to generate an imaging beam (e.g., x-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, imaging system 2000 represents a 4D CT scanner as discussed above. In one embodiment, diagnostic imaging system 2000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data such as the 4D CT data discussed above. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing the operations of the methods discussed herein that, for example, may be loaded in processing device 3010 from storage 3030 and/or system memory 3020.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and data, for example, the 4D CT data discussed above. Storage device 3030 may also be used for storing instructions for performing the treatment planning methods discussed herein.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and target regions delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

It should be noted that the described treatment system 1700 is only representative of an exemplary system. Other embodiments of the system 1700 may have many different configurations and architectures and may include fewer or more components.

Figure 9:
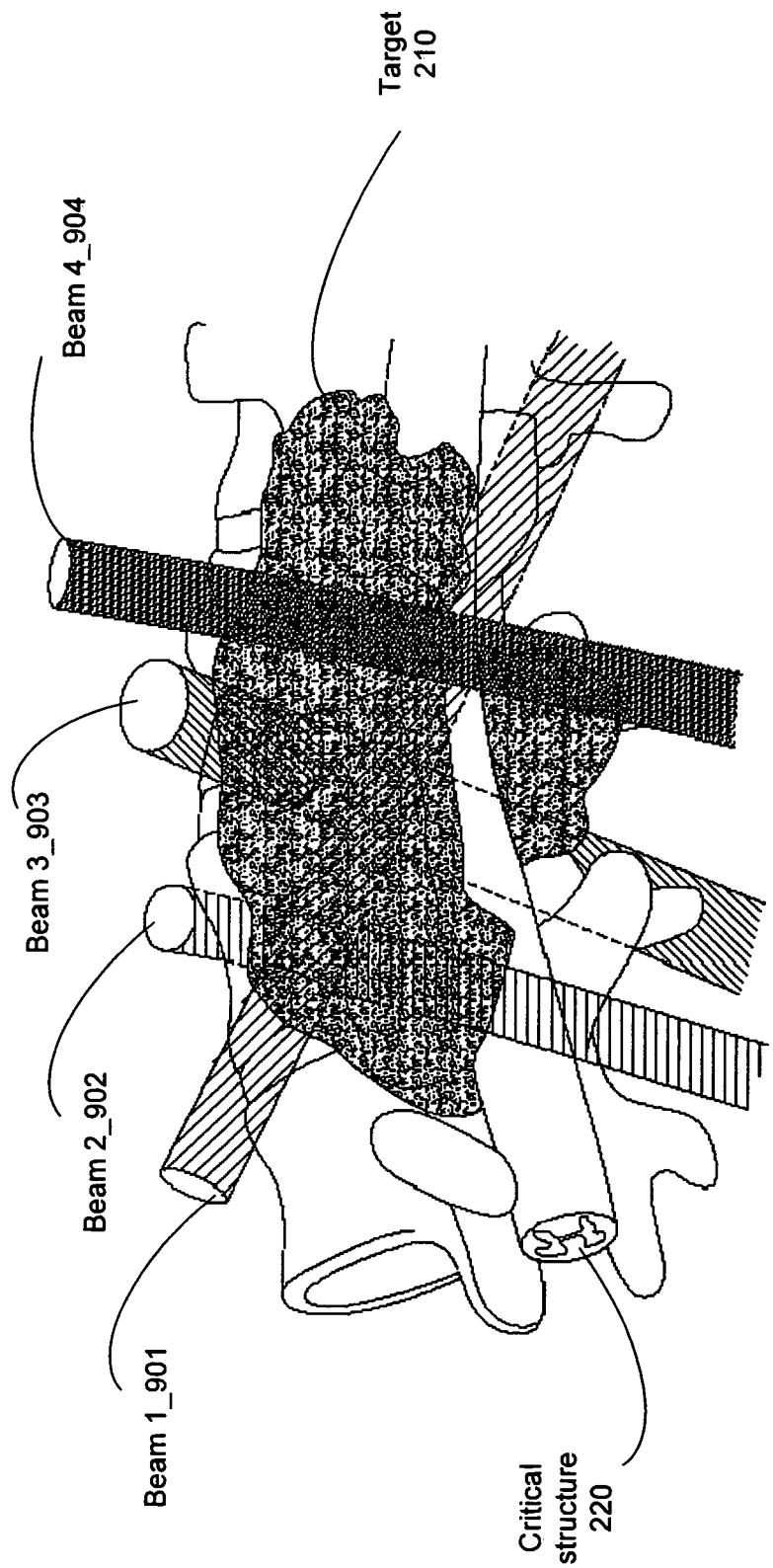
FIG. 9 illustrates a three-dimensional perspective view of beam delivery for one embodiment of a radiation treatment process.
Figure 11:
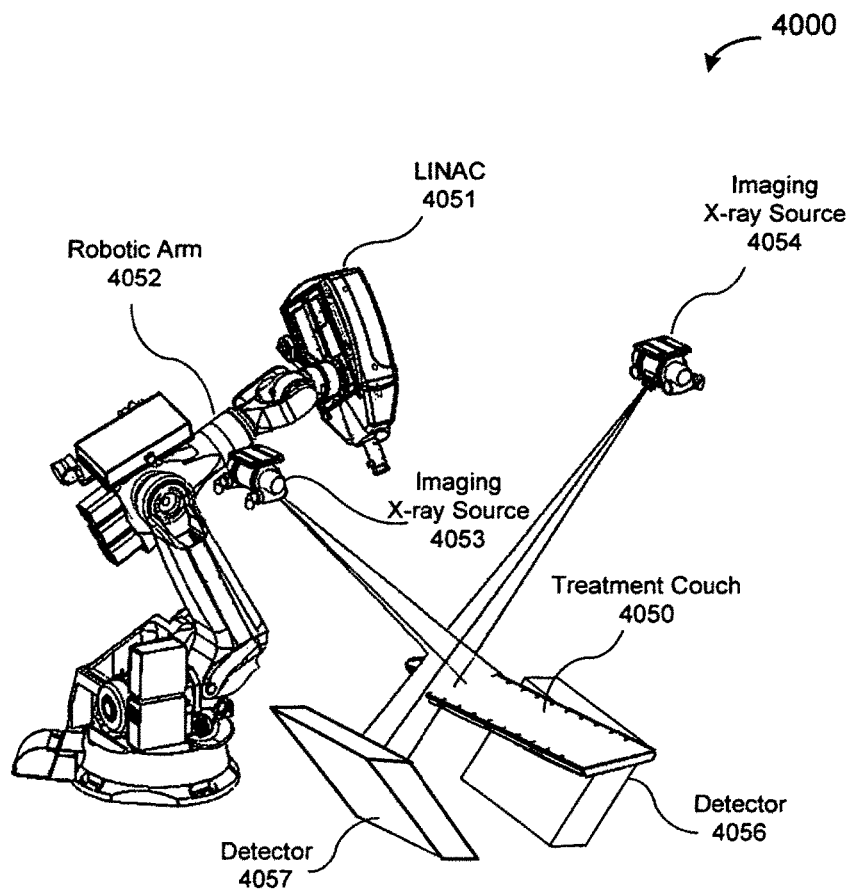
FIG. 11 illustrates one embodiment of an image-guided, robotic-based radiation treatment system.

In one embodiment, as illustrated in FIG. 11, treatment delivery system 4000 may be an image-guided, robotic-based radiation treatment system (e.g., for performing radio-surgery) such as the CYBERKNIFE® system developed by Accuray, Incorporated of California. In FIG. 11, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target region or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target region as illustrated in FIG. 9). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 11, imaging system 4020 may be represented by X-ray sources 4053 and 4054 and X-ray image detectors (imagers) 4056 and 4057. In one embodiment, for example, two x-ray sources 4053 and 4054 may be nominally aligned to project imaging x-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each x-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch developed by Accuray Incorporated of California, or be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the effectuation of an operation controlled by the treatment planning system, such as the application of a beam (e.g., radiation, acoustic, etc.) and "target" may refer to a non-anatomical object or area.

Embodiments of the present invention include various operations, which are described herein. These operations may be performed by hardware components, software, firmware, or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within an iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
    receiving four-dimensional diagnostic imaging data generated by an imaging device; and
    developing a radiation treatment plan using the four-dimensional diagnostic imaging data, wherein the four-dimensional diagnostic imaging data comprises a plurality of three-dimensional images, and wherein each of the plurality of three-dimensional images represents a different point in a motion cycle, and wherein developing the radiation treatment plan comprises:
        receiving delineated target region information;
        defining a motion model describing a motion of the target region over a motion cycle using the four-dimensional diagnostic imaging data as input data to the motion model;
        obtaining a set of deformation fields for the target region using a set of vectors derived from the plurality of three-dimensional images;
        deriving an effective depth vector along a central axis of the plurality of treatment beams for each of the plurality of images;
        assigning a weight to each of the plurality of three-dimensional images according to an estimate of a portion of time the target region spends in each part of the motion cycle to generate a dose estimate that takes the motion into account, and wherein the dose distribution to the target region is further calculated using the set of deformation fields, the effective depth vector for each of the plurality of images and the weight of each of the plurality of three-dimensional images;
        calculating a dose distribution over the motion cycle to the target region from a plurality of treatment beams of the radiation treatment plan using the motion model that takes the motion into account;
        optimizing the radiation treatment plan using the motion model by modifying beam parameters of the plurality of treatment beams such that the calculated dose distribution is optimized for a set of user-specified objectives; and outputting the optimized radiation treatment plan to a treatment delivery system.

2. The method of claim 1, wherein the motion of the target region is a deformation due to respiratory motion, the motion cycle is a respiratory cycle, and the motion model is a deformation model.

3. The method of claim 1, wherein the delineated target region information is on at least one of the plurality of three-dimensional images.

4. The method of claim 1, wherein the four-dimensional diagnostic imaging data is four-dimensional computed tomography (CT) data.

5. The method of claim 4, wherein one or more of the plurality of three-dimensional images has an anatomical structure delineated thereon.

6. The method of claim 4, wherein the radiation treatment plan comprises a conformal plan.

7. The method of claim 4, wherein the target region is delineated on a CT image acquired during patient breath hold.

8. The method of claim 1, wherein the dose distribution is referred to a reference CT image being one of the plurality of three-dimensional images using the motion model.

9. The method of claim 1, wherein defining the motion model comprises performing a non-rigid registration of the plurality of three-dimensional images.

10. The method of claim 1, wherein the weight is calculated using a table or formula.

11. The method of claim 1, wherein the weight is derived from a priori motion data measured for the patient.

12. The method of claim 1, wherein optimizing comprises constructing a dose mask for each of the plurality of treatment beams using the motion model.

13. The method of claim 1, wherein optimizing comprises calculating a standard dose mask using the reference image.

14. The method of claim 1, further comprising performing a review of the treatment plan after optimization to compare the dose distribution taking into account effects of respiratory motion with another dose distribution ignoring the effects.

15. A non-transitory machine readable medium having instructions thereon, which instructions, when executed by a digital processing device, cause the digital processing device to perform the following, comprising:
receiving four-dimensional diagnostic imaging data generated by an imaging device;
developing, at least in part, a radiation treatment plan using the four-dimensional diagnostic imaging data, wherein the four-dimensional diagnostic imaging data comprises a plurality of three-dimensional images, and wherein each of the plurality of three-dimensional images represents a different point in a motion cycle, and wherein developing the radiation treatment plan comprises:
receiving information delineating a target region;
defining a motion model describing a motion of the target region over a motion cycle using the four-dimensional diagnostic imaging data as input data to the motion model;
obtaining a set of deformation fields for the target region using a set of vectors derived from the plurality of three-dimensional images;
deriving an effective depth vector along a central axis of the plurality of treatment beams for each of the plurality of images;
assigning a weight to each of the plurality of three-dimensional images according to an estimate of a portion of time the target region spends in each part of the motion cycle to generate a dose estimate that takes the motion into account, and wherein the dose distribution to the target region is further calculated using the set of deformation fields, the effective depth vector for each of the plurality of images and the weight of each of the plurality of three-dimensional images;
calculating a dose distribution over the motion cycle to the target region from a plurality of treatment beams of the radiation treatment plan using the motion model that takes the motion of the target into account;
optimizing the radiation treatment plan using the motion model by modifying beam parameters of the plurality of treatment beams such that the calculated dose distribution is optimized for a set of user-specified objectives; and
outputting the optimized radiation treatment plan to a treatment delivery system.

16. The machine readable medium of claim 15, wherein the weight is calculated using a table or formula.

17. The machine readable medium of claim 15, wherein the weight is derived from a priori motion data measured for the patient.

18. The machine readable medium of claim 15, wherein optimizing comprises constructing a dose mask for each of the plurality of treatment beams using the motion model.

19. The machine readable medium of claim 15, wherein optimizing comprises calculating a standard dose mask using the reference image.

20. The machine readable medium of claim 15, further having instructions thereon to perform the following comprising generating another dose distribution that does not take into account the motion of the target region.

21. The machine readable medium of claim 15, wherein optimizing comprises optimizing the dose distribution.

22. The machine readable medium of claim 15, wherein the four-dimensional diagnostic imaging data is four-dimensional computed tomography (CT) data.

23. An apparatus, comprising:
a storage device to store four-dimensional diagnostic imaging data generated by an imaging device; and
a processor operatively coupled to the storage device, the processor to:
receive the four-dimensional diagnostic imaging data; and
develop a radiation treatment plan using the four-dimensional diagnostic imaging data, wherein the four-dimensional diagnostic imaging data comprises a plurality of three-dimensional images, and wherein each of the plurality of three-dimensional images represents a different point in a motion cycle, and wherein to develop the radiation treatment plan, the processor is configured to:
receive information delineating a target region;
define a motion model describing a motion of the target region over the motion cycle using the four-dimensional diagnostic imaging data as input data to the motion model;
obtain a set of deformation fields for the target region using a set of vectors derived from the plurality of three-dimensional images;
derive an effective depth vector along a central axis of the plurality of treatment beams for each of the plurality of images;

assign a weight to each of the plurality of three-dimensional images according to an estimate of a portion of time the target region spends in each part of the motion cycle to generate a dose estimate that takes the motion into account, and wherein the dose distribution to the target region is further calculated using the set of deformation fields, the effective depth vector for each of the plurality of images and the weight of each of the plurality of three-dimensional images;

calculate a dose distribution to the target region from a plurality of treatment beams using the motion model that takes the motion of the target into account;

optimize the radiation treatment plan using the motion model by modifying beam parameters of the plurality of treatment beams such that the calculated dose distribution is optimized for a set of user-specified objectives; and output the optimized radiation treatment plan to a treatment delivery system.

24. The apparatus of claim 23, wherein the four-dimensional diagnostic imaging data is four-dimensional computed tomography (CT) data.

25. The apparatus of claim 24, further comprising a four-dimensional CT imaging system to generate the four-dimensional CT data, wherein the processor is operatively coupled to receive the four-dimensional CT data from the four-dimensional CT imaging system.

26. The apparatus of claim 23, further comprising a radiation source to deliver radiation treatment to the target region according to the radiation treatment plan.

27. The apparatus of claim 23, wherein each of the plurality of three-dimensional images represents a different point in the motion cycle.

28. The apparatus of claim 26, further comprising a treatment delivery imaging system to track an actual position of the target region relative to a radiation beam path produced by the radiation beam source during delivery of the radiation treatment plan.

29. The apparatus of claim 26, wherein the radiation source comprises a linear accelerator (LINAC) mounted to a robotic arm.

30. The apparatus of claim 26, wherein the radiation source comprises a linear accelerator (LINAC) mounted to a gantry.

31. The apparatus of claim 30, wherein the LINAC is mounted on a gimbaled head assembly.

\* \* \* \* \*